United States Patent [19]

Brooks

[11] Patent Number: 5,360,793
[45] Date of Patent: Nov. 1, 1994

[54] RAFTING ANTACID FORMULATION

[75] Inventor: William J. Brooks, Gateshead, England

[73] Assignee: Sterling Winthrop Inc., New York, N.Y.

[21] Appl. No.: 66,824

[22] Filed: May 24, 1993

[51] Int. Cl.⁵ .................. A61K 31/70; A61K 31/715; A61K 33/08
[52] U.S. Cl. ....................... 514/23; 514/54; 514/819; 424/689; 424/690
[58] Field of Search .............. 424/686, 690, 717, 689; 514/54, 819, 23

[56] References Cited

U.S. PATENT DOCUMENTS

| | | | |
|---|---|---|---|
| 2,755,220 | 7/1956 | Alford | 514/54 |
| 2,774,710 | 12/1956 | Thompson | 424/690 |
| 2,999,790 | 9/1961 | Alford | 424/690 |
| 3,272,704 | 9/1966 | Beckman | 424/690 |
| 4,012,333 | 3/1977 | Towle | 514/54 |
| 4,140,760 | 2/1979 | Withington | 424/81 |
| 4,163,777 | 8/1979 | Mitra | 424/690 |
| 4,465,667 | 8/1984 | Byrod et al. | 424/690 |
| 4,613,497 | 9/1986 | Chaukin | 424/44 |
| 4,744,986 | 5/1988 | Luber et al. | 514/54 |
| 4,869,902 | 9/1989 | Buhler et al. | 424/686 |
| 5,023,245 | 6/1991 | Kuhrts | 514/54 |
| 5,036,057 | 7/1991 | Martin | 514/54 |
| 5,068,109 | 11/1991 | Foldager et al. | 514/819 |
| 5,112,813 | 5/1992 | Luber et al. | 514/54 |
| 5,147,655 | 9/1992 | Ibsen | 424/489 |

FOREIGN PATENT DOCUMENTS 8504806 11/1985 WIPO .

OTHER PUBLICATIONS

N. Washington et al *Int. J. Pharm.* 27 279–286 (1985).
N. Washington et al. *Int. J. Pharm* 28 139–143 (1986).

*Primary Examiner*—Raymond J. Henley, III
*Attorney, Agent, or Firm*—Richard A. Hake; Paul E. Dupont

[57] ABSTRACT

This invention is an antacid composition capable of forming a floating gelatinous mass when contacted with aqueous acid and consisting essentially of, as active ingredients, xanthan gum; an effective acid neutralizing amount of hexitol stabilized aluminum hydroxide and a gas producing material capable of producing a non-toxic gas when contacted with aqueous acid which may be formulated as a solid, powder, tablet or suspension.

17 Claims, No Drawings

RAFTING ANTACID FORMULATION

BACKGROUND OF THE INVENTION a) Field of the Invention

The present invention relates to pharmaceutical compositions and particularly to compositions for use in treating gastroesophageal and gastrointestinal irritations.

Esophageal pain, commonly referred to as heartburn, is symptomatic of gastric reflux. Gastric reflux occurs when small amounts of gastric juice and/or bile acids pass into the lower part of the esophagus and cause esophageal irritation. Typically, gastric reflux, which occurs after meals, especially large meals, is aggravated by bending over or lying down, and is a common occurrence in patients having a hiatal hernia, or a weakening of the esophageal sphincter. Severe episodes of gastric reflux may inflame the esophageal mucosa and lead to the more serious condition of reflux esophagitis in which severe damage or loss of squamous epithelium of the lower part of the esophagus may occur.

The invention relates to raft-forming preparations which are employed for the treatment and alleviation of painful conditions resulting from the reflux of gastric acid and bile into the esophagus, comprising aluminum hydroxide, xanthan gum and bicarbonate or carbonate, as the antacid and raft forming components.

b) Information Disclosure Statement

Basic metal salts and their use in antacid formulations are known in the art. Examples of metals known to form basic salts are alkali or alkaline earth metals and aluminum. The most commonly employed aluminum salts are the hydroxide, carbonate or phosphate. Examples of alkaline earth metals such as calcium are known, the use of calcium carbonate as an antacid either alone or in combination with other metal salts, such as magnesium carbonate and magnesium hydroxide is known. The use alkali metals, such as sodium as sodium bicarbonate is known in antacid formulations.

An approach to the problem of gastric reflux comprises the administration of a preparation which forms a gelatinous foam or raft which floats on the stomach contents. The foam-containing antacid precedes the stomach contents into the esophagus when reflux occurs and helps to protect the mucosa from further irritation. The gelatinous foam is formed by the combination of an acid insoluble gelatinous material entrapping $CO_2$ gas. The present invention relates to improvements in formulation of preparations which are capable of forming such foams.

Antacid compositions which contain a gel-forming agent and an acid neutralizing agent are known (cf.N. Washington et al. *Int. J. Pharm.* 27, 1985, pp. 279–286 and N. Washington et al., *Int. J. Pharm.* 28, 1986, pp.139–143). The gel-forming agent in these known compositions is alginic acid, and they further contain sodium bicarbonate and usually at least one other acid neutralizing agent as well.

Typically when alginate-based calcium carbonate/sodium bicarbonate containing rafting antacids come into contact with the acid contents of the stomach the water insoluble calcium carbonate dissolves, liberating calcium ions which then react with alginate to form a gelatinous mass of calcium alginate. Much of the carbon dioxide liberated from the calcium carbonate and from the sodium bicarbonate becomes trapped in the mass causing it to rise as a 'raft' of neutral gel which effectively impedes reflux. In severe cases this neutral gel itself may be refluxed into the esophagus, where it is said to protect the inflamed mucosa, allowing healing to take place and preventing further inflammation.

Several formulations have been developed in order to produce an antacid suspension with rafting properties, combining antacid placement in the upper stomach/lower esophagus with prolonged buffering ability to ensure that refluxed material is close to neutral pH. Heretofore known preparations used to create the aforementioned "rafts" comprise sodium bicarbonate and either solid compositions or liquid suspensions of alginic acid or its sodium salt. Exemplary of such prior art preparations include the product sold under the trade name GAVISCON (Marion Laboratories) and compositions described in U.S. Pat. No. 4,140,760.

GAVISCON is a pink, viscous, aniseed-flavored suspension. 10 ml of GAVISCON contains 500 mg sodium alginate, 267 mg sodium bicarbonate and 160 mg calcium carbonate. The recommended dose is 10–20 ml four times a day, after meals and at bedtime, or as needed.

In addition certain compositions for raft forming antacids are disclosed in the following U.S. patents:

U.S. Pat. No. 5,112,813 issued to Rhone-Poulenc Rorer on May 12, 1992 describes a process for producing a viscosity-stable rafting antacid composition using potassium bicarbonate, magnesium carbonate, aluminum hydroxide, magnesium alginate and xanthan gum as a stabilizer.

U.S. Pat. No. 5,068,109 issued to Farina Foods on Nov. 26, 1991 describes an antacid composition with floating properties containing potassium bicarbonate, magnesium carbonate and pectin.

U.S. Pat. No. 5,036,057 issued to University of Melbourne on Jul. 30, 1991 describes a method of treating gastroesophageal reflux using a composition with rafting properties containing calcium carbonate, sodium bicarbonate, aluminum hydroxide or magnesium carbonate and sodium alginate.

U.S. Pat. No. 4,869,902 issued to Rorer Pharmaceutical Corporation on Sep. 26, 1989 describes a pharmaceutical composition for treatment of reflux using a composition with rafting properties containing calcium carbonate, sodium bicarbonate, aluminum hydroxide or magnesium carbonate and sodium alginate.

U.S. Pat. No. 4,744,986 issued to Rorer Pharmaceutical Corporation May 17, 1988 describes a pharmaceutical composition for treatment of reflux esophagitis with rafting properties containing potassium bicarbonate, magnesium carbonate, aluminum hydroxide, stabilizer and magnesium alginate.

U.S. Pat. No. 4,613,497 issued to Health Products Development, Inc. on Sep. 23, 1986 describes a dry, water-foamable pharmaceutical composition for a gastric antacid material producing rafting containing carrageenan, sodium bicarbonate, tartaric acid, calcium carbonate, aluminum hydroxide and magnesium hydroxide.

U.S. Pat. No. 4,465,667 issued to Aktielbolaget Hassle on Aug. 14, 1984 describes a processing for preparing gastric acid neutralizing agents having rafting properties containing magnesium carbonate, hexitol stabilized aluminum hydroxide, and hydrogenated glucose polymers.

U.S. Pat. No. 4,012,333 issued to Hercules Incorporated on Mar. 15, 1977 describes preparation of gels of beta-1,3-glucan-type polysaccharide by exposure to $CO_2$ gas.

U.S. Pat. No. 4,140,760 issued to Reckitt & Colman Products Limited on Feb. 20, 1979 describes a pharmaceutical composition for treatment of reflux esophagitis with rafting properties containing potassium bicarbonate, magnesium carbonate, and sodium alginate.

U.S. Pat. No. 2,774,710 issued to Kenneth Thomson on Dec. 18, 1956 describes an antacid preparation combining known antacids and a composition producing a protective layer containing a guar gum.

SUMMARY OF THE INVENTION

The present invention relates to an antacid composition capable of forming a floating gelatinous mass when contacted with aqueous acid and consisting essentially of, as active ingredients, xanthan gum; an effective acid neutralizing amount of hexitol-stabilized aluminum hydroxide and a gas producing material capable of producing a non-toxic gas when contacted with aqueous acid.

The invention also relates to a method for neutralizing an excess of acid in gastric juice and a method for preventing esophageal reflux thereof in mammals, including man, and a method for the treatment of hyperacidity and disorders related thereto, comprising administering a gastric acid neutralizing amount of a composition as described above.

DETAILED DESCRIPTION INCLUSIVE OF PREFERRED EMBODIMENTS

It is one object of the present invention to provide an antacid preparation which combines the antacid effects of the known antacids with the property of forming a protective layer of excellent adhesiveness to the gastric and duodenal mucosa whereby the viscosity and adhesiveness of said layer are not impaired by increasing activity of the stomach and which does not give rise to acid rebound secretion.

Other objects of this invention and advantageous features thereof will become apparent as the description proceeds.

The invention utilizes xanthan gum as a raft forming agent. The amount of xanthan gum must be sufficient to form a stable "raft", but in a small enough quantity to allow suspensions thereof to remain pourable. Typically this amount is about 0.01% to about 4% by weight of the suspension. Xanthan gum has been used in the prior art solely as a bulking agent or stabilizer. However, we have found xanthan gum to be useful as a raft former in antacid formulation. Xanthan gum is a high molecular weight natural polysaccharide and is well known in the art and commercially available. Varying viscosity grades of xanthan gum are known in the art. (Cf. Colegrove et al., U.S. Pat. No. 4,874,854).

The antacid component comprises hexitol-stabilized aluminum hydroxide, or a combination thereof, with other known antacids, in an amount useful to neutralize stomach acid and form a stable raft with the xanthan gum. Typically this amount is about 0.05% to about 6.0% by weight of the formulation. The novel formulation utilizes the ability of hexitol-stabilized aluminum hydroxide, preferably polyhydroxy-aluminum-monocarbonate-hexitol (alexitol), which does not thicken upon standing in formulation, to produce a viscous mass when mixed with xanthan gum under acidic conditions. Alexito's properties are discussed in Alford, U.S. Pat. No. 2,999,790 (1962 to Sterling Drug), incorporated herein by reference. It is a tasteless, odorless powder, useful in formulating antacids.

A gas-producing material is present in an amount so as to provide an adequate volume of gas to float the gelatinous mass formed when the composition is contacted with the gastric contents. In the preferred embodiment, this gelatinous mass is rendered buoyant by the inclusion of alkali or alkaline metal carbonates or bicarbonates in the formulation. The carbonate or bicarbonate reacts with stomach acids to release carbon dioxide which in turn becomes trapped in the viscous mass, making it buoyant. An alkali or alkaline earth metal carbonate may also be included to provide additional buffering capacity.

The antacid of the invention can be formulated as a powder, tablet, suspension or other suitable form known in the art. Such formulations can be prepared by conventional methods known in the art.

The preferred embodiment is a gastric acid neutralizing suspension, comprising hexitol stabilized aluminum hydroxide in an amount corresponding to about 0.05% to about 6.0% by weight to volume (w/v) and as a "raft" forming compound, xanthan gum, in an amount of about 0.1% to about 4% w/v, and an acid activated gas forming agent providing sufficient gas to provide the raft with bouyancy as described above, a bulking agent, and water.

The bulking agent should be pharmaceutically acceptable and, in addition to providing appropriate bulk to the antacid formulation, have properties which will contribute to the palatability of the formulation. Suitable bulking agents are well known in the pharmaceutical formulating art. Preferably the bulking agent is a sweetener such as a sugar, e.g., sucrose, and/or a polyhydric alcohol, e.g., mannitol, sorbitol, glucose, maltose, fructose, and xylitol, and/or a mixture thereof. A preferred bulking agent is sucrose. The bulking agent is employed in an amount of from about 5% to about 50% by weight, preferably from about 15% to about 25% by weight of the active ingredients.

A particularly preferred embodiment of the invention provides a raft forming antacid formulation as a suspension, consisting essentially of, as active ingredients, from about 0.5% to about 3.0% w/v of alexitol, preferably alexitol sodium and from about 0.5% to about 4% w/v of xanthan gum, and a nontoxic gas forming agent, preferably in a sufficient amount to give between about 0.5% and about 3.0% of gas, preferably carbon dioxide, when reacted under acid conditions. If the gas is carbon dioxide, generally the gas forming agent will be present in an amount from about 1.5 % to about 6.0% w/v, and is generally an alkali or alkaline earth metal bicarbonate and/or carbonate salt.

If desired, additional gastric acid neutralizing agents such as aluminum carbonate, magnesium hydroxide, magnesium carbonate, calcium carbonate, magnesium oxide, sodium bicarbonate, and the like, may be present. Adjusting buffering capacity of an antacid is conventional in the art and is well within the skill of the practitioner in the art.

It is preferred that the aqueous suspensions of the present invention have a long shelf life and not be subject to deterioration by microorganisms. Consequently the liquid compositions may contain a preservative. Examples of preservatives include esters of parahydroxybenzoates and their salts, myacide, cetyl pyridinium chloride, quaternary ammonium salts and the like. Antioxidants may also be included in the suspension to prevent discoloration over time.

The compositions of the present invention may also include one or more sweetening or flavoring agents to enhance palatability. Suitable sweeteners include sucrose, xylitol, dextrose, fructose, glucose, mannitol, isomalt, aspartame, acesulfame potassium, saccharin, calcium saccharin and thaumatin.

Colorants may also be employed to enhance the appearance of the product. Such colorants include titanium dioxide and other pharmaceutically acceptable colorants. It will be understood by those skilled in the art that pharmaceutically inert excipients, diluents and the like can be included in the compositions as desired.

Preparation of the antacid formulation follows standard methods currently used in the art for formulating solid, tablet, and suspension antacids.

WORKING EXAMPLES

The following examples further illustrate the invention but do not limit it thereto.

The individual carbon dioxide producing components were calculated to give formulations where the percentage of $CO_2$ w/v theoretically liberated was in a range which would give bouyancy to the raft.

Percent carbon dioxide is calculated in the following examples as shown:
Potassium bicarbonate has 44.0% w/v of $CO_2$, that is 1 g of potassium bicarbonate will neutralize 100 ml of 0.1M HCl. Thus, 1 g of potassium bicarbonate will liberate 0.44 g of carbon dioxide, i.e. 44.0% $CO_2$. Magnesium carbonate has 37.0% of w/v of $CO_2$. Thus the % w/v $CO_2$ figures for formulations are obtained by taking the corresponding percentage of each of the above figures multiplied by the amount of gassing agents used to give a % w/v of $CO_2$ for each of the formulations, expressed as % w/v (g/100 ml).

The individual antacid substances used in example formulations were calculated to have corresponding total acid neutralizing capacity (TANC) values commensurate with their purpose as an antacid. TANC is calculated by using the ingredient's neutralizing capacities in the same manner as % w/v $CO_2$.

| ANTACID | TANC |
| --- | --- |
| Alexitol powder | 225 ml 0.1 M HCl/g |
| Potassium bicarbonate | 100 ml 0.1 M HCl/g |
| Magnesium carbonate | 211 ml 0.1 M HCl/g |

The percent w/v figures are obtained by taking the corresponding percentage of each of the above ingredients multiplied by the ingredient's neutralizing capacity to give a TANC value for each formula, expressed as ml of 0.1M HCl/20 ml dose.

EXAMPLE I

| FORMULATION | GRAMS |
| --- | --- |
| Active Ingredients | |
| Alexitol sodium | 18 |
| Sodium bicarbonate | 54 |
| Xanthan gum | 7.2 |
| Other Ingredients | |
| Sorbitol syrup | 360 |
| Nipastat ™ | 2 |
| Saccharin sodium | 1.8 |
| Glycerol | 180 |
| Titanium dioxide | 1.8 |
| Mint-chocolate flavoring | 2 |
| Purified water | 1000 |

Example I was prepared as follows:

A. Water and the sorbitol were mixed. To this mixture all soluble components, sodium saccharin, preservatives and bicarbonates were added and mixed.

B. Xanthan gum and glycerol were mixed together, then titanium dioxide was added and mixed until smooth. This mixture was added to mixture A with stirring. To this mixture alexitol sodium and bicarbonates were added and the mixture homogenized.

Color and flavor were added to the batch and it was diluted to volume.

EXAMPLE II

| | Quantity (g/20 ml dose) |
| --- | --- |
| Active Ingredients | |
| Alexitol sodium | 0.30 |
| Potassium bicarbonate | 0.60 |
| Magnesium carbonate | 0.10 |
| Xanthan gum | 0.18 |
| Other Ingredients | |
| Sorbitol solution | 4.0 |
| Nipacombin SK ™ | 0.024 |
| Cetylpyridinium chloride | 0.02 |
| Sodium saccharin | 0.01 |
| Glycerol | 2.00 |
| Titanium dioxide | 0.02 |
| Spearmint flavoring | 0.01 |
| Purified water | 14.536 |

Example II was prepared as follows:

The formulation has a 1.51% weight to volume (% w/v) $CO_2$ content and a calculated total acid neutralizing capacity (TANC) of 149 ml of 0.1M HCl/20 ml dose.

Sorbitol and glycerol were included as bulking agents. Sodium saccharin, spearmint flavor and titanium dioxide were included to enhance the flavor and appearance of the product. The suspension was prepared using high shear agitation under vacuum.

Using the method and Other Ingredients of Example II, the following example formulations, using differing levels of active ingredients, were prepared:

| Active Ingredient | Ex. 3 | 4 | 5 | 6 | 7 |
| --- | --- | --- | --- | --- | --- |
| Xanthan gum | 0.9 | 0.9 | 0.9 | 0.9 | 0.9 |
| Alexitol sodium | 1.0 | 1.2 | 1.5 | 1.0 | 1.0 |
| Potassium bicarbonate | 3.0 | 3.0 | 3.0 | 3.5 | 4.0 |
| Magnesium carbonate | 1.0 | 0 | 1.0 | 1.0 | 1.0 |
| % $CO_2$ | 1.69 | 1.69 | 1.69 | 1.91 | 2.13 |
| TANC | 147 | 156 | 170 | 157 | 167 |

The in vitro neutralization and rafting properties of antacid suspensions based on xanthan gum and alexitol have been investigated using a modified version of the Rossett and Rice test, using a common liquid base, (Rossett NE and Rice NL: An in vitro evaluation of the efficacy of more frequently used antacids with particular attention to tablets. *Gastroenterology*, 1954, 26, 490–495). The test was run in a 150 ml beaker containing 125 ml of 0.03M HCl. An inlet tube was suspended near the side of the beaker, with the outlet near the bottom of the vessel. The tube was supplied with 0.1M HCl, pumped from a reservoir at a constant rate. An outlet was placed opposite the inlet tube and was pumped at the same rate as the inlet so as to maintain a constant volume in the beaker. A pH electrode was suspended into the reaction vessel so that the bulb and pore were covered. Contents of the beaker were stirred by a magnetic stirring devise. The glass beaker was temperature controlled to 37°±1° C. in a small water bath.

pH readings were taken when the electrode pore was just covered, except for the reading taken at 40 minutes.

Photographs were taken at T=5, 15, 35 and 38 minutes during the experiment.

The test proceeded as follows:

T=O min: The sample was injected centrally into the 125 ml of 0.03M hydrochloric acid while very rapid stirring was taking place. Rapid stirring was continued.

T=1 min: Simultaneously a pH reading was taken, the stirring rate reduced to approximately 100 rpm, and the stirring rate reduced to approximately 100 rpm, and the pump started to pump in 0.1M hydrochloric acid at 4 ml/min into the beaker and the outlet at the same rate. pH readings were subsequently taken every minute until T=30 min.

T=30 min: A pH reading was taken, and the pump and stirrer were stopped.

T=35 min: After the photograph had been taken, the stirrer rate was adjusted to maximum.

T=38 min: After the photograph had been taken, the stirrer was stopped.

T=40 min: A pH measurement was taken below the raft.

Raft Forming, pH and Stability

In each formulation, a large 'plug' formed very quickly, acting as an effective antacid raft. The pH was maintained at about 6 for the duration of the experiment.

The test formulations performed well, the rafts formed from all of the formulations of the invention had good resistance to agitation, and accordingly are unlikely to break up in the stomach.

Formulations of the invention had in-raft pH values that were in the region of 6–7.

The practitioner in the art can prepare antacids of the invention of suitable viscosity, raft formation and buffering capacity in dosages and dosage forms suitable for mammalian, and especially human, consumption.

What is claimed is;

1. An antacid composition capable of forming a floating gelatinous mass when contacted with aqueous acid and consisting essentially of, as active ingredients, xanthan gum; an effective acid neutralizing amount of hexitol-stabilized aluminum hydroxide and a gas producing material capable of producing a non-toxic gas when contacted with aqueous acid.

2. A rafting antacid formulation, according to claim 1, wherein xanthan gum forms a gelatinous mass with hexitol stabilized aluminum hydroxide upon contact with acid and such gelatinous mass obtains bouyancy by means of an alkali or alkaline metal carbonate or bicarbonate in an effective gas volume producing amount to provide such bouyancy.

3. A rafting antacid formulation, according to claim 2, having;

0.5 to 6.0 percent by weight hexitol stabilized aluminum hydroxide 0.05 to 4 percent by weight xanthan gum 0.1 to 3 percent by weight carbonate ion, in the form of an alkali or alkaline metal carbonate or bicarbonate.

4. A rafting antacid formulation, according to claim 3, having;

0.5 to 3.0 percent by weight stabilized aluminum hydroxide 0.1 to 1.8 percent by weight xanthan gum 0.1 to 1.8 percent by weight carbonate ion, in the form of an alkali or alkaline metal carbonate or bicarbonate 5 to 50 percent by weight bulking agent, and water.

5. A rafting antacid formulation, according to claim 4, further comprising a preservative.

6. A rafting antacid formulation, according to claim 5, further comprising a sweetener and flavoring.

7. A rafting antacid formulation, according to claim 6, further comprising a colorant.

8. An antacid according to claim 7 consisting essentially of:

0.3 g of alexitol sodium;

0.6 g of potassium bicarbonate;

0.1 g of magnesium carbonate;

0.18 g of xanthan gum 4.0 g sorbitol;

0.44 g of a preservative;

0.01 g of sodium saccharin;

2.0 g of glycerol;

0.02 g of titanium dioxide;

0.01 g of spearmint flavoring; and 14.536 g of purified water per 20 ml dose.

9. A method for the treatment of hyperacidity and disorders related thereto, comprising administering to the patient suffering therefrom a gastric acid neutralizing amount of a composition according to claim 1.

10. A method for the treatment of hyperacidity and disorders related thereto, comprising administering to the patient suffering therefrom a gastric acid neutralizing amount of a composition according to claim 3.

11. A method for the treatment of hyperacidity and disorders related thereto, comprising administering to the patient suffering therefrom a gastric acid neutralizing amount of a composition according to claim 8.

12. A method of treating gastric reflux in a patient in need of such treatment, comprising administering to said patient an effective gastric reflux suppressive amount of a composition according to claim 1.

13. A method of treating gastric reflux in a patient in need of such treatment, comprising administering to said patient an effective gastric reflux suppreslye amount of a composition according to claim 2.

14. A method of treating gastric reflux in a patient in need of such treatment, comprising administering to said patient an effective gastric reflux suppreslye amount of a composition according to claim 3.

15. A method of treating gastric reflux in a patient in need of such treatment, comprising administering to said patient an effective gastric reflux suppreslye amount of a composition according to claim 4.

16. A method of treating gastric reflux in a patient in need of such treatment, comprising administering to said patient an effective gastric reflux suppreslye amount of a composition according to claim 7.

17. A method of treating gastric reflux in a patient in need of such treatment, comprising administering to said patient an effective gastric reflux suppreslye amount of a composition according to claim 8.

* * * * *